United States Patent [19]

Schubert

[11] Patent Number: 4,920,212

[45] Date of Patent: Apr. 24, 1990

[54] PROCESS FOR THE PREPARATION OF (ARYL)-(DIMETHYL)-(3-(4-FLUORO-3-ARYLOXYPHENYL)PROPYL)SILANES

[75] Inventor: Hans H. Schubert, Frankfurt am Main, Fed. Rep. of Germany

[73] Assignee: Hoechst Aktiengesellschaft, Frankfurt am Main, Fed. Rep. of Germany

[21] Appl. No.: 245,404

[22] Filed: Sep. 16, 1988

[30] Foreign Application Priority Data

Sep. 19, 1987 [DE] Fed. Rep. of Germany ....... 3731609

[51] Int. Cl.$^5$ ................................................ C07F 7/08
[52] U.S. Cl. .................................................. 549/214
[58] Field of Search ................ 556/447, 427; 549/214

[56] References Cited

U.S. PATENT DOCUMENTS

| | | | |
|---|---|---|---|
| 2,914,548 | 11/1959 | Schroll | 556/447 |
| 3,013,044 | 12/1961 | Schnabel | 556/447 |
| 3,637,866 | 1/1972 | De Pasquale et al. | 260/612 R |
| 4,481,365 | 11/1984 | Förster et al. | 556/447 X |
| 4,709,068 | 11/1987 | Sieburth | 556/447 |

FOREIGN PATENT DOCUMENTS 0224024 of 0000 European Pat. Off. ........ 556/447 R UX

*Primary Examiner*—Paul F. Shaver
*Attorney, Agent, or Firm*—Curtis, Morris & Safford

[57] ABSTRACT

The present invention relates to a process for the preparation of compounds of the formula I

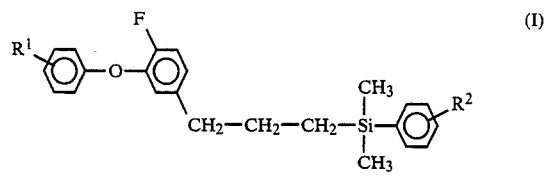

in which
$R^1$ denotes H, halogen, $(C_1-C_4)$-alkyl or $(C_1-C_4)$-alkoxy and
$R^2$ denotes H, halogen, $(C_1-C_4)$-alkyl, $(C_1-C_4)$-alkylthio, $(C_1-C_4)$-alkoxy or the bivalent group 3,4-0-$CH_2$-O, comprising reacting a compound of the formula II

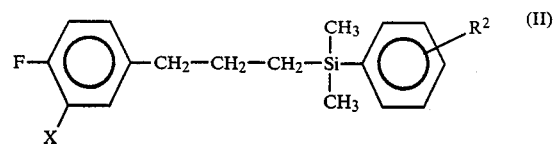

in which X denotes halogen and $R^2$ has the meaning as in formula I, in the presence of a copper catalyst with an alkali metal phenolate or alkaline earth metal phenolate of the formula III

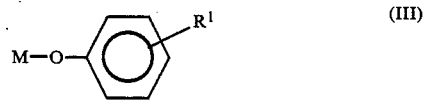

in which M denotes an alkali metal or an alkaline earth metal and $R^1$ has the meaning as in formula I.

6 Claims, No Drawings

PROCESS FOR THE PREPARATION OF (ARYL)-(DIMETHYL)-(3-(4-FLUORO-3-ARYLOXY-PHENYL)PROPYL)SILANES

The present invention relates to a process for the preparation of compounds of the formula I

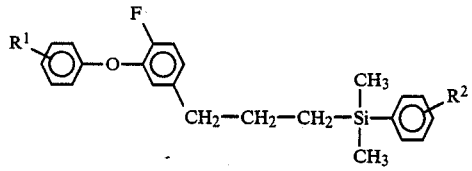

in which
$R^1$ denotes H, halogen, $(C_1-C_4)$-alkyl or $(C_1-C_4)$-alkoxy and
$R^2$ denotes H, halogen, $(C_1-C_4)$-alkyl, $(C_1-C_4)$-alkylthio, $(C_1-C_4)$-alkoxy or the bivalent group 3,4-O—$CH_2$—O, which comprises reacting a compound of the formula II

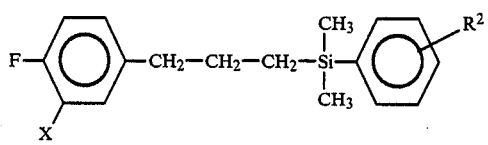

in which X denotes halogen and $R^2$ has the meaning as in formula I, in the presence of a copper catalyst with an alkali metal phenolate or alkaline earth metal phenolate of the formula III

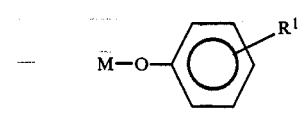

in which M denotes an alkali metal or an alkaline earth metal and $R^1$ has the meaning as in formula I.

Preferably, X denotes Cl in the compounds of the formula II.

The compounds of the formulae I and II are known and have significance as insecticidal, acaricidal and nematocidal active compounds (EP-A-0,224,024).

The previously known synthetic routes to the compounds of the formula I states out, for example, from olefins of the formula A which are difficult to prepare

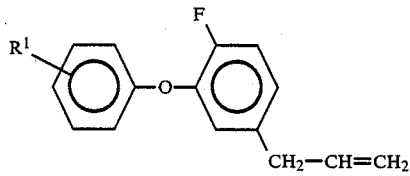

in which $R^1$ has the meaning as in formula I, as educts which are then converted into the corresponding silanes of the formula I by hydrosilylation (EP-A-0,224,024).

The stating compounds of the formula II of the process according to the invention can be obtained selectively and in which yields from the corresponding allylbenzenes of the formula B

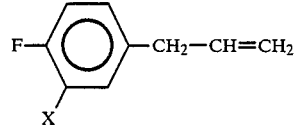

in which X denotes halogen, by reaction with a silane of the formula C

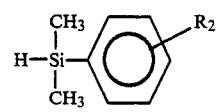

in which $R^2$ has the meaning as in formula I, in the presence of a complex compound of an element of subgroup VIII of the periodic table as the catalyst. This reaction as well as the preparation of the compounds of the formula B starting out from suitable organometallic intermediates are likewise described in EP-A-0,224,024.

An additional, very simple route for the preparation of the compounds of the formula B alternatively exists. The synthesis starts out from 3-chloro-4-fluoroaniline, or from 3-bromo-4-fluoroaniline or 3-iodo-4-fluoroaniline which are easily obtainable from 4-fluoroaniline by halogenation in the presence of a "swamp-catalyst" ($AlCl_3$/HCl gas). Preferably, in this case, the bromo or chloro compound is used, particularly preferably the bromo compound. The diazonium salts obtainable from these adducts can be alkylated in good yields under reducing conditions using acrolein to give 3-phenyl-propanals of the formula D

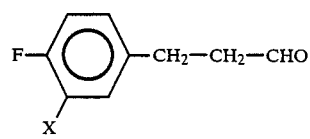

in which X denotes halogen.

Reductive amination thereof (for example reaction with dimethylamine and hydrogen in the presence of a catalyst or with dimethylformamide and formic acid) yields the 3-arylpropyl-dimethylamines of the formula E

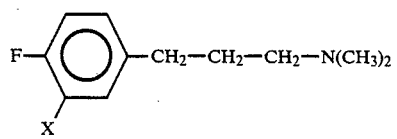

in which X denotes halogen. These are converted by $H_2O_2$ or peracids into the corresponding amine oxides, from which the compounds of the formula B then result by pyrolysis.

Collectively, the compounds of the formula II used as starting materials for the process according to the invention and all precursors necessary for their preparation can be prepared in close dependence on reactions known from the literature:

A. Citterio, Org. Synth. 62, 67 (1984); E. Möler, R. Schröter, Methoden der org. Chemie (Houben-Weyl) Vol. XI/1, 648–664, (1957); A. C. Cope, C. L. Bumgardner, J. Amer. Chem. Soc. 79, 960 (1957)); see Methoden der org. Chemie (Houben-Weyl), Vol. XIII/5, Georg Thieme Verlag, Stuttgart 1980; E. Pfeil, Angew. Chem. 65, 155–158 (1953); H. H. Hodgson, Chem. Rev. 40, 251–277 (1947); H. Fricke, Methoden der org. Chemie (Houben-Weyl), Vol. V/1b, 465–476 (1972).

Starting with the compounds of the formula II, the formation of the compounds of the formula I, which proceeds selectively and with good yields, was particularly surprising in the process according to the invention. In contrast to other reactions of fluorohaloaromatics with phenolates which are known from the literature, in which the fluorine and not the other halogen is preferably exchanged (compare DE-OS 2,619,489, US-PS 3,637,866), the less electronegative halogen can be substituted smoothly, in particular in the case of the bromofluoro and iodofluoroaromatics of the formula II. The selective reaction of the chlorofluoroaromatics of the formula II in non-basis solvents was particularly surprising, since non-activated chloroaromatics usually only enter into the copper salt-catalyzed phenoxylation in the presence of basic solvents such as pyridine or quinoline (R. G. Bacon, H. A. Hill, J. Chem. Soc. 1964, 1108). In other cases, the presence of a co-catalyst is necessary (G. Soula, J. Org. Chem. 50, 3717 (1985)).

The best yields are attained in the process according to the invention when the reaction is carried out in weakly polar, aprotic solvents such as, for example, polyethylene glycol dialkyl ethers at temperatures between 100° C. and 255° C., the optimum temperature range and the solvent being varied with the halogen to be replaced.

Whereas the iodofluoroaromatic of the formula II can be brought to reaction in diethylene glycol dimethyl ether at temperatures of 100°–160° C., preferably at 130°–160° C., higher-boiling solvents such as, for example, triglyme or tetraglyme and temperatures of 190°–255° C., preferably 220°–250° C., are necessary for the reaction of the chlorofluoroaromatic. The bromofluoroaromatic reacts with phenolates at temperatures of 145°–210° C., preferably at 145°–190° C., for example in diglyme or triglyme, but also in diethylene glycol diethyl ether.

The reaction of the compounds of the formula II with those of the formula III takes place in the presence of a catalyst which contains copper in various oxidation states. The oxidation states $Cu^0$ and $Cu^{1+}$ are preferred. Examples of such a catalyst are copper powder, copper(I) oxide, copper(I) chloride and copper(I) bromide, of which copper(I) oxide, copper(I) chloride and copper(I) bromide are preferably used.

1–1.6 moles, preferably 1–1.4 moles, of an alkali metal phenolate or an alkaline earth metal phenolate, preferably a sodium phenolate or a potassium phenolate, are employed per mole of a halofluoroaromatic of the formula III. The necessary amount of copper catalyst generally varies between 1–20 g. The working up of the reaction product (compound of the formula I) takes place in a customary manner, for example by filtering, diluting the filtrate with a solvent which is non-miscible with water and washing the solution with dilute sodium hydroxide solution and water. After drying and filtering, the solvent is removed by evaporation and the residue is distilled under vacuum.

The process according to the invention is illustrated by the following examples:

WORKING EXAMPLES

A. Preparation of a compound of the formula B (1) 145.6 g (1.00 mol) of 3-chloro-4-fluoroaniline were dissolved in a mixture of 330 ml of 48% strength hydrobromic acid and 330 ml of water and diazotized by adding a solution of 70.4 g (1.02 mol) of sodium nitrite in 220 ml of water dropwise at 5° C. The diazonium salt solution thus obtained was added dropwise to a mixture of 188 g (1.3 mol) of copper(I) bromide and 400 ml of 48% strength hydrobromic acid at 30°–40° C. After conclusion of gas evolution, the produce was extracted using three 300 ml portions of hexane. The extracts were washed twice with 5N sodium hydroxide solution and once with water, dried over sodium sulfate and evaporated. The residue yielded 187.2 g (89%) of 4-bromo-2-chlorofluorobenzene of $b.p._{10}=73°–75°$ C. with a purity of >99% (determined by gas chromatography) on subsequent distillation.

(2) The corresponding arylmagnesium bromide was prepared from 406 g (1.94 mol) of 4-bromo-2-chlorofluorobenzene and 48.6 g (2.00 mol) of magnesium turnings in 1,300 ml of anhydrous tetrahydrofuran by the customary process. The solution thus obtained was added dropwise to a solution of 278.3 g (2.3 mol) of allyl bromide in 200 ml of anhydrous tetrahydrofuran at 30°–45° C. The mixture was then heated under reflux for 0.5 h, allowed to stand at room temperature for 16 h and poured onto 1.5 liters of ice-water. After acidification using a little 2N hydrochloric acid, the mixture was extracted twice using 1 liter of hexane each time. The extracts were washed three times with water, dried over $Na_2SO_4$ and evaporated. The residue yielded 235 g (71%) of 3-(3-chloro-4-fluorophenyl)propene of $b.p._{10}=72°$ C. with a purity of 98.7% (determined by gas chromatography) on subsequent distillation.

B. Preparation of a compound of the formula II

Three drops of a 30% strength solution of hexachloroplatinic acid in isopropanol were added with the aid of a pipette to a mixture of 234 g (1.37 mol) of 3-(3-chloro-4-fluorophenyl)propene and 261 g (1.45 mol) of (4-ethoxyphenyl)dimethylsilane. After a short time, an exothermic reaction took place and the mixture warmed to about 130° C. After cooling, the product was distilled in vacuo. 392 g (82%) of (4-ethoxyphenyl)-(dimethyl)-(3-(3-chloro-4-fluorophenyl)propyl)silane were obtained as a colorless oil of $b.p._{0.1}=165°–170°$ C., the purity of which was determined to be 97.4% by gas chromatography.

C. Preparation of a compound of the formula I

A mixture of 456.2 g (1.30 mol) of (4-ethoxyphenyl)-(dimethyl)-(3-(3-chloro-4-fluorophenyl)propyl)silane, 232.2 g (2.00 mol) of sodium phenolate, 13 g of copper(I) chloride and 500 ml of tetraglyme was heated to 240°–255° C. for 1.5 h. After cooling the reaction mixture to 90° C., a larger part of the solvent was removed by distillation at 90°–140° C. internal temperature and 0.4 Torr (about 400 g). The crude product was then stirred at room temperature with 500 ml of 2N sodium hydroxide solution and extracted twice using 800 ml of hexane each time. The organic extracts were washed five times with 300 ml of water each time, dried over sodium sulfate and evaporated. The crude product thus obtained (486.1 g/92%) was distilled over a 50 cm split tube column. 233 g (44%) of (4-ethoxyphenyl)-(dimethyl)-(3-(4-fluoro-3-phenoxyphenyl)propyl)silane were obtained as a colorless oil of b.p.$_{0.04}$=208°-212° C., the purity of which was determined to be 95.2% by gas chromatography.

I claim:

1. A process for the preparation of a compound of formula I

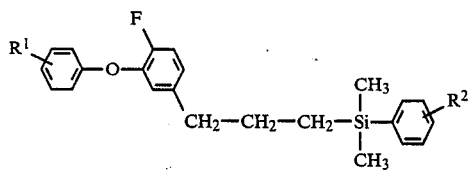

in which:

R$^1$ is hydrogen, halogen, (C$_1$-C$_4$)-alkyl or (C$_1$-C$_4$)-alkoxy; and

R$^2$ is hydrogen, halogen, (C$_1$-C$_4$)-alkyl, (C$_1$-C$_4$)-alkyl-thio, (C$_1$-C$_4$)-alkoxy or the bivalent group 3,4-O—CH$_2$—O;

which comprises reacting a compound of formula II

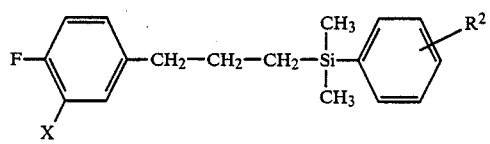

in which:

X is chlorine, bromine or iodine; and

R$^2$ has the meaning as in formula I;

in the presence of a copper catalyst with an alkali metal phenolate or alkaline earth metal phenolate of formula III

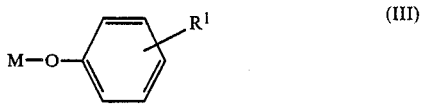

in which:

M is an alkali metal or an alkaline earth metal; and

R$^1$ has the meaning as in formula I.

2. The process as claimed in claim 1, wherein X is Cl in formula II.

3. The process as claimed in claim 1, wherein the compound of formula II is reacted with the compound of formula III between 100° C. and 255° C.

4. The process as claimed in claim 1, wherein a polyethylene glycol dialkyl ether is used as solvent for the reaction of the compound of formula II with the compound of formula III.

5. The process as claimed in claim 1, wherein the copper catalyst is selected from the group consisting of CuCl, CuBr and Cu$_2$O.

6. The process as claimed in claim 2, wherein the reaction of the compounds of formulae II and III is carried out in a non-basic solvent without a co-catalyst.

* * * * *